(12) United States Patent
Waluszko

(10) Patent No.: US 7,081,637 B2
(45) Date of Patent: Jul. 25, 2006

(54) ULTRAVIOLET LIGHTING PLATFORM

(76) Inventor: Alex Waluszko, 2066 W. 11th St., Upland, CA (US) 91786

( * ) Notice: Subject to any disclaimer, the term of this patent is extended or adjusted under 35 U.S.C. 154(b) by 131 days.

(21) Appl. No.: 10/851,308

(22) Filed: May 21, 2004

(65) Prior Publication Data
US 2005/0127303 A1 Jun. 16, 2005

Related U.S. Application Data

(63) Continuation-in-part of application No. 10/733,561, filed on Dec. 10, 2003.

(51) Int. Cl.
*H01J 1/62* (2006.01)

(52) U.S. Cl. .............. 250/504 R; 250/455.11; 422/24

(58) Field of Classification Search ............ 250/504 R, 250/455.11; 313/493, 634; 362/230, 231; 422/24
See application file for complete search history.

(56) References Cited

U.S. PATENT DOCUMENTS 5,914,560 A * 6/1999 Winsor ................. 313/493

* cited by examiner

*Primary Examiner*—Kiet T. Nguyen
(74) *Attorney, Agent, or Firm*—James E. Brunton, Esq.

(57) ABSTRACT

A method and apparatus for genomic or proteomic research to visualize fluorescent labeled DNA, RNA or protein samples that have been separated for documentation and analysis. The apparatus includes a novel radiation source for uniformly irradiating the samples which comprises a grid constructed from a continuous, serpentine shaped ultraviolet light producing tube that is strategically formed to provide a multiplicity of side-by-side, immediately adjacent irradiating segments. In one form of the invention the apparatus also includes a first conversion plate that is carried by the housing at a location intermediate the radiation source and the sample supporting platform for converting the radiation emitted from the source to radiation at a second wavelength.

24 Claims, 13 Drawing Sheets

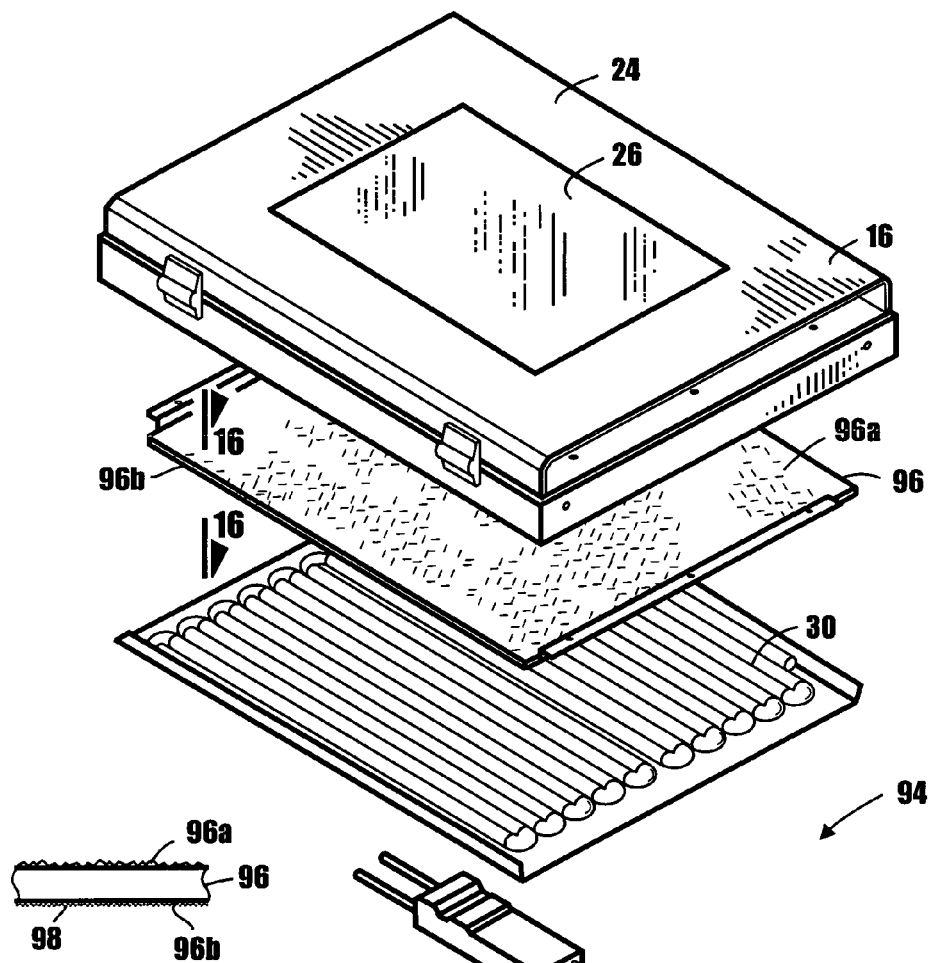
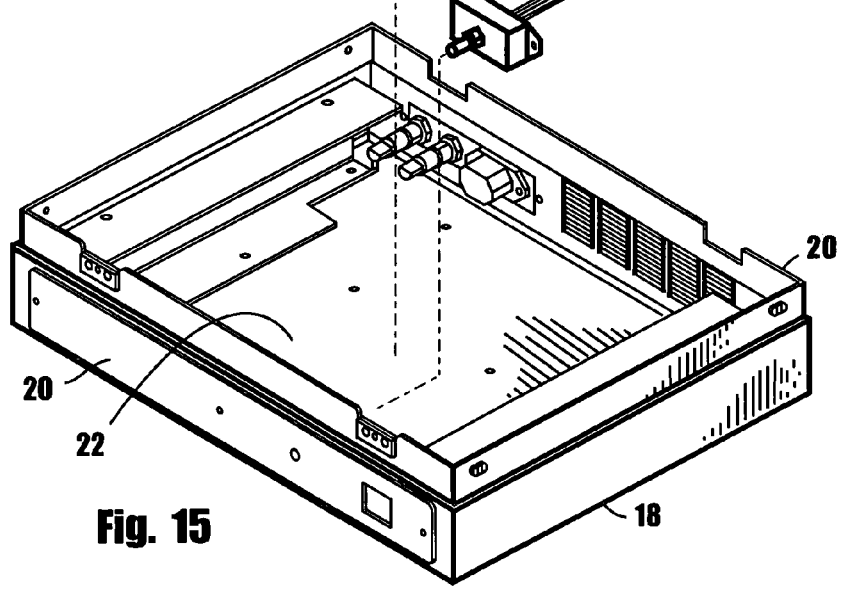
Fig. 16
Fig. 15

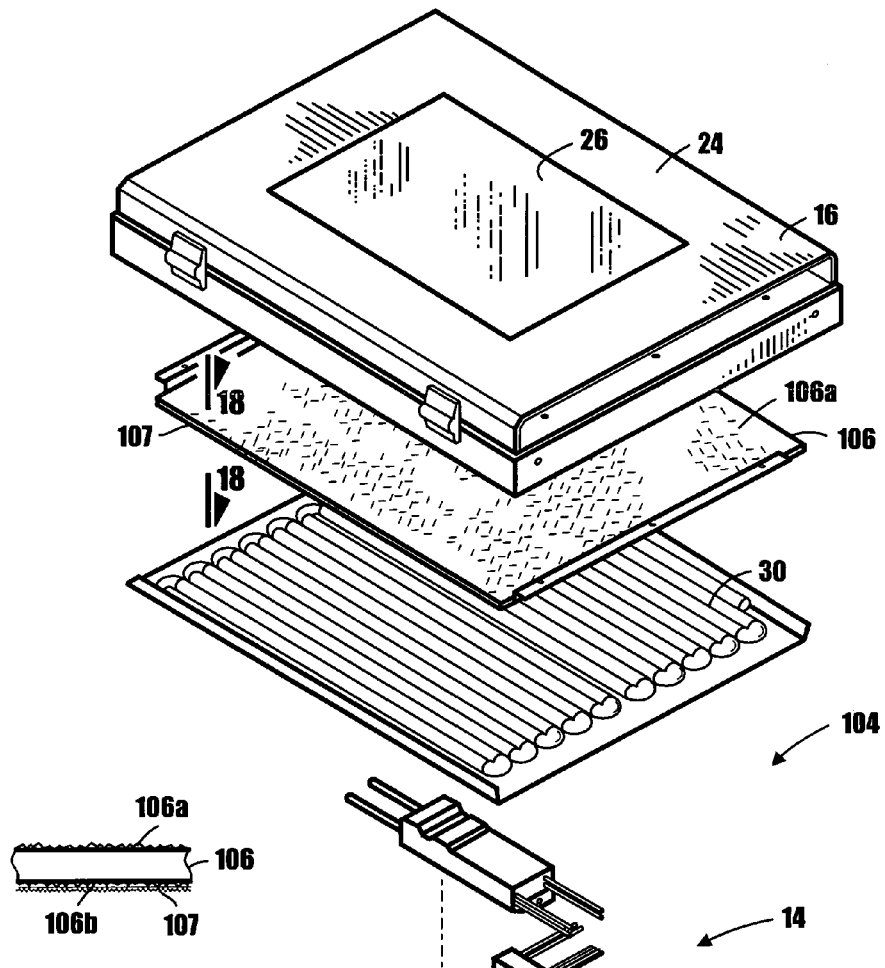
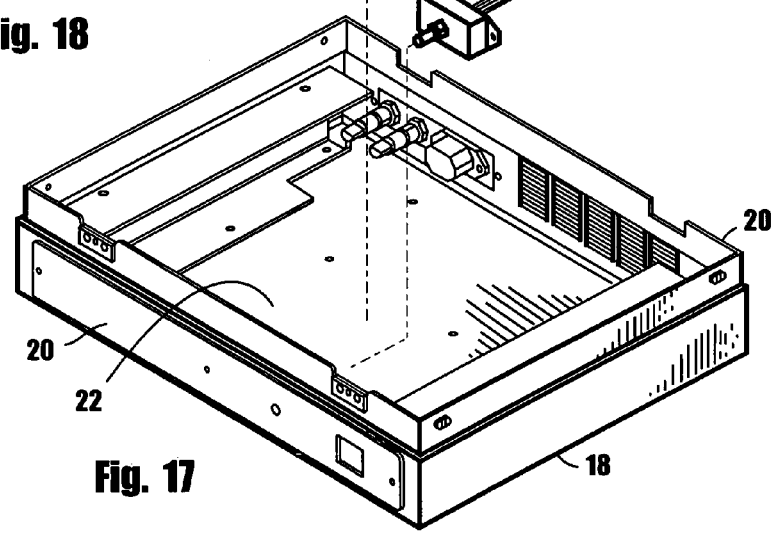
Fig. 18
Fig. 17

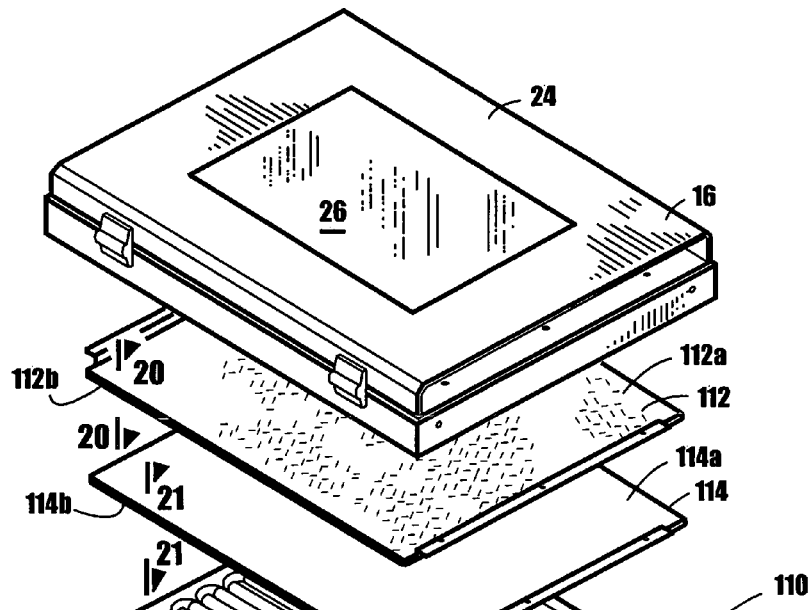
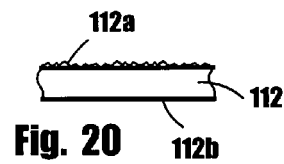
Fig. 20
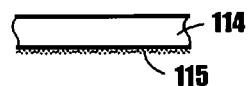
Fig. 21
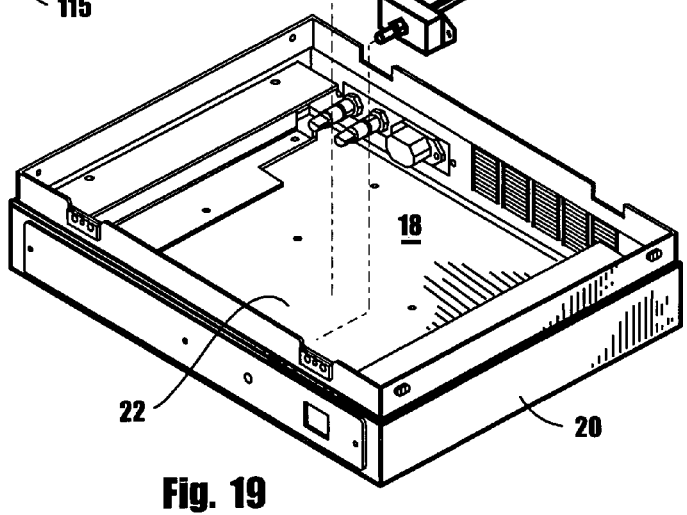
Fig. 19

ULTRAVIOLET LIGHTING PLATFORM

This is a Continuation-In Part of co-pending U.S. Ser. No. 10/733,561 filed Dec. 10, 2003.

BACKGROUND OF THE INVENTION

1. Field of the Invention

The present invention relates generally to ultraviolet radiation devices. More particularly, the invention concerns an apparatus for use in genomic or proteomic research to visualize fluorescent labeled DNA, RNA or protein samples that have been separated for documentation and analysis.

2. Discussion of the Prior Art

By way of brief background, ultraviolet light (UV), which is electromagnetic radiation in the region of the spectrum located between X-rays and visible light, is typically divided into three principal ranges, namely long wave, mid-range, and short wave. For each of these UV ranges specific applications have been developed.

As a general rule, the desired ultraviolet wavelength is obtained from a fluorescent style tube that is an electric discharge device that uses a low-pressure mercury vapor arc to generate ultraviolet energy. The ultraviolet energy released in typical, commercially available fluorescent tubes is primarily at the wavelength of about 254 nanometers.

However, the fluorescent tubes can be modified to release other ultraviolet wavelengths by the use of phosphors, which have the ability to absorb the ultraviolet energy and re-radiate it in other wavelengths. For example, long wave ultraviolet of about 365 nanometers and mid-range ultraviolet of about 300 nanometers are created by coating the inside of the fluorescent tubes with the proper phosphors which convert the short wave ultraviolet.

In the past ultraviolet irradiation of selected articles has been accomplished using a single UV range fluorescent tube mounted within a suitable enclosure. In order to eliminate white light generated by the UV tube, some prior art devices make use of a UV transmitting ambient or visible light blocking filter that is typically mounted in front of the UV tube.

By way of example, U.S. Pat. No. 5,175,347 issued to the present inventor describes an apparatus for irradiating an object such as a specimen of material with ultraviolet radiation at a selected long, short or mid-wave length. Similarly, U.S. Pat. No. 3,936,186 issued to Boland et al. discloses an apparatus for exposing diazo printing plates and the like of the character that are used in the graphic arts field. In like manner, U.S. Pat. No. 5,288,647 issued Zimlich, Jr. et al. relates to a method by which polynucleotide specimens can be irradiated particularly for the purpose of fixing them to a substrate. Similarly, U.S. Pat. No. 5,736,744 issued to Johannsen et al. in which the present inventor is named as a coinventor, discloses a wave length shifting filter separate and apart from a transilluminator. The wavelength shifting filter uses phosphors in a flat array to provide a selection of visible wavelengths.

U.S. Pat. No. 5,951,838 issued to Heffelfinger et al., concerns a method and apparatus for achieving uniform illumination of an electrophoresis apparatus. In the Heffelfinger et al. method, uniform illumination is achieved by scanning the light source across the sample gel in a direction perpendicular to the axis of the source. The light source is comprised of one or more light bulbs placed in a light tray. Variations in light intensity near the source end portions is minimized using a variety of techniques including extended light bulbs, filters, reflectors, and diffusers, or supplemental sources.

The standard prior art method for separating, identifying and purifying biological samples is electrophoresis through a gel. The electrophoresis process is simple and well understood today. It is commonly used in one dimension separation where distinct bands of distinct biologicals are formed, or in two dimension separation where distinct spots or bands are formed.

Generally, following the process of electrophoretic separation, the separated biological samples are stained with a fluorescent dye, such as ethidium bromide. A set of multiple visible fluorescing dyes can be utilized that are capable of identifying specifically separated biological samples. These dyes have the ability to specifically attach (tag) themselves to specific biological samples and fluoresce in different visible wavelengths.

After the sample is dyed it is exposed to an ultraviolet radiation source, normally within the spectral bandwidth of mid-range ultraviolet (280 nm–320 nm). This range generally provides for the best and brightest wave shift conversion of the dye. During exposure, the dye labeled, separated biological sample is visible for viewing, documentation and further analysis. It is to be noted that other wavelengths of ultraviolet, such as short wave ultraviolet (generally considered as 254 nm), long wave ultraviolet (320–400 nm), broadband ultraviolet and a combination of short wave, mid-range and long wave can also be used to generate the fluorescent wave shift action of the dyes.

Although excitation of the fluorescent labeled biological sample is at times possible with visible wavelengths and light boxes that generate visible wavelengths, such as 420 nm or 480 nm, it is generally understood that UV excitation allows larger stoke shifts (that is the discrimination between excitation and emission wavelengths), enables higher signal to noise ratios and provides greater sensitivity.

A commonly used prior art tool for illuminating electrophoretically separated gels is the ultraviolet transilluminator (light box). These light boxes, generally comprise a single wavelength set of ultraviolet producing fluorescent lamps. These lamps are generally horizontally mounted within the light box behind a window upon which the dye labeled sample rests. The window typically comprises an ultraviolet transmitting, ambient (visible) light blocking filter material. Other ultraviolet light boxes are commercially available that provide dual UV wavelength combinations of 254 nm/365 nm, 254 nm/1302 nm and 365 nm/1302 nm. In this regard, commercially available mid-range ultraviolet light boxes interchangeably use the wavelength designations 300 nm, 302 nm, 310 nm or 312 nm, since the UV bandwidth output of these wavelength designations is substantially the same. Additionally, UV light boxes are commercially available that provide all three UV wavelengths of 254 nm, 302 nm and 365 nm. However, substantially all presently commercially available ultraviolet transilluminators (light boxes) use commercially available ultraviolet producing lamps that singly provide UV wavelengths in 365 (UV-A bandwidth), 302 nm (UV-B bandwidth) and 254 nm (UV-C bandwidth).

Another device used to capture fluorescent labeled biological samples is commercially available from Bio-Rad, Inc. of Hercules, Calif. under the name and style FLUOR S MULTIMAGER. This device uses a single broadband (290 nm–365 nm) ultraviolet fluorescent lamp. This ultraviolet fluorescent style tube lamp is horizontally mounted below the sample holding window and is typically scanned across the sample permitting the acquisition of the fluorescent signal via a charge coupled device (CCD) based camera system. This configuration limits the actual viewing of the fluorescent labeled sample by the researcher in real-time. The previously mentioned U.S. Pat. No. 5,951,838 issued to Heffelfinger, et al. and entitled "Method and Apparatus for Correcting Illumination Non-Uniformities" describes this method in greater detail.

As a general rule, all commercially available ultraviolet light boxes use 4, 5, or 6 fluorescent style UV generating lamps. These UV fluorescent lamps (254 nm, 302 nm, 365nm or broadband) are typically commercially available in 4 watt, 6 watt, 8 watt, 15 watt and 25 watt styles and in varying lengths. The lamps are normally configured in a horizontal pattern and are generally superimposed over a reflective aluminum reflector. Typically, a UV transmitting-ambient visible light blocking filter is positioned above the lamps.

It is well understood that conventional ultraviolet generating fluorescent style tube lamps of the type described in the preceding paragraph generate ultraviolet radiation in an arc formed between the electrodes in the lamp. However it is not well known that the intensity or output of this type of lamp diminishes from the center point of the arc towards the arc origination points. Accordingly, in virtually all wattages and configurations, the presently commercially available lamps provide a sample illumination surface that is substantially non-uniform. This problem of non-uniform UV illumination of fluorescent biologically labeled samples has been addressed in the past by the development of data manipulation and correction software that is specially designed to account for UV background on a fluorescent labeled sample. A description of such software and of its use is discussed in detail in U.S. Pat. Nos. 5,951,838 and 5,897,760 issued to Heffelfinger, et al.

Other prior art devices suggest the use of a cold cathode type serpentine grid to generate a more uniform visible light for use in LCD and photographic film viewing background lighting. A description of such prior art devices can be found in U.S. Pat. Nos. 5,731,658 and 6,069,441 issued to Lengyel et al.

Commercially available alternatives to the ultraviolet light box are available in devices that use lasers to illuminate the fluorescent labeled biological samples. Typically, these devices rely on laser light sources to illuminate the fluorescent "tagged" samples to excite the samples. In such devices, the laser source is scanned serially to excite each sample.

As will be better understood from the discussion that follows, the present invention overcomes many of the drawbacks of the prior art devices.

SUMMARY OF THE INVENTION

The present invention provides a method and apparatus for use in genomic or proteomic research to visualize fluorescent labeled DNA, RNA or protein samples that have been separated for documentation and analysis. By way of summary, one form of the apparatus of the invention comprises a housing having interconnected top, bottom and side walls defining an internal chamber and a sample supporting platform having a sample supporting area and radiation means disposed within the chamber for uniformly irradiating the sample supporting area with ultraviolet light at a first wavelength. The radiation means uniquely comprises a grid for emitting ultraviolet radiation constructed from a continuous, serpentine shaped ultraviolet tube that is strategically formed to provide a multiplicity of side-by-side, immediately adjacent irradiating segments. In one form of the invention the apparatus also includes a first conversion means that is removably carried by the housing at a location intermediate the radiation means and the sample supporting platform for converting the radiation emitted from said source of ultraviolet radiation to radiation at a second wavelength.

With the foregoing in mind, it is an object of the present invention to provide a method and apparatus in which the uniformity of excitation radiation with across the sample supporting surface of the apparatus is vastly improved when compared the nonuniformity of radiation across the sample supporting surface of prior art transilluminators. More particularly, if it is an object of the invention to provide apparatus of the character described in which the Coefficient of Variation is well below about 5 to 10%.

Another object of the invention is to provide a method and apparatus of the character described in the preceding paragraphs in which meaningful, quantitative side by side comparisons of samples are possible.

Another object of the invention is to provide a method and apparatus in which sequential analysis of several samples is greatly simplified and is substantially more accurate than is possible with prior art transilluminators because of the minimal effect on excitation intensity of sample positioning on the sample support surface. More particularly, it is an object of the invention to provide a method and apparatus in which the same sample will give similar fluorescent intensities regardless of where the sample is placed on the sample supporting surface of the apparatus.

Another object of the invention is to provide a novel radiation source for uniformly irradiating a spaced apart surface with an ultraviolet radiation, the radiation source comprising a uniquely configured grid constructed from a continuous, serpentine shaped ultraviolet tube.

Another object of the invention is to provide a novel radiation source for uniformly irradiating a spaced apart surface with an ultraviolet radiation, the radiation source comprising a base having machined therein a plurality of interconnected, top open channels, a top plate over laying the base and cooperating therewith to form a plurality of closed channels and a gaseous medium such as mercury and argon contained within the closed channels.

Another object of the invention is to provide an apparatus which includes a novel dispersion means that is disposed intermediate the radiation source and the sample supporting platform and functions to uniformly disperse the radiation generated by the radiation source in a manner to significantly contribute to the uniform illumination of the sample supporting platform of the apparatus of the invention.

Another object of the invention is to provide an apparatus of the character described in the immediately preceding paragraph in which the dispersion means comprises a quartz fibrous mesh.

Another object of the invention is to provide an apparatus of the character described in the preceding paragraphs in which the dispersion means comprises a glass platform having an upper and lower surface at least one of which is abraided, or roughened in a manner to uniformly disperse the radiation generated by the radiation source.

The foregoing as well as other objectives of the invention will become apparent from the description which follows:

BRIEF DESCRIPTION OF THE DRAWINGS

FIG. 15 is a generally perspective, exploded view of still another form of the apparatus of the invention for uniformly illuminating molecular samples with ultraviolet radiation.

FIG. 16 is a fragmentary cross-sectional view taken along lines 16—16 of FIG. 15.

FIG. 17 is a generally perspective, exploded view of yet another form of the apparatus of the invention for uniformly illuminating molecular samples with ultraviolet radiation.

FIG. 18 is a fragmentary cross-sectional view taken along lines 18—18 of FIG. 17.

FIG. 19 is a generally perspective, exploded view of still another form of the apparatus of the invention for uniformly illuminating molecular samples with ultraviolet radiation.

FIG. 20 is a fragmentary cross-sectional view taken along lines 20—20 of FIG. 19.

FIG. 21 is a fragmentary cross-sectional view taken along lines 21—21 of FIG. 19.

DESCRIPTION OF THE INVENTION

Figure 1:
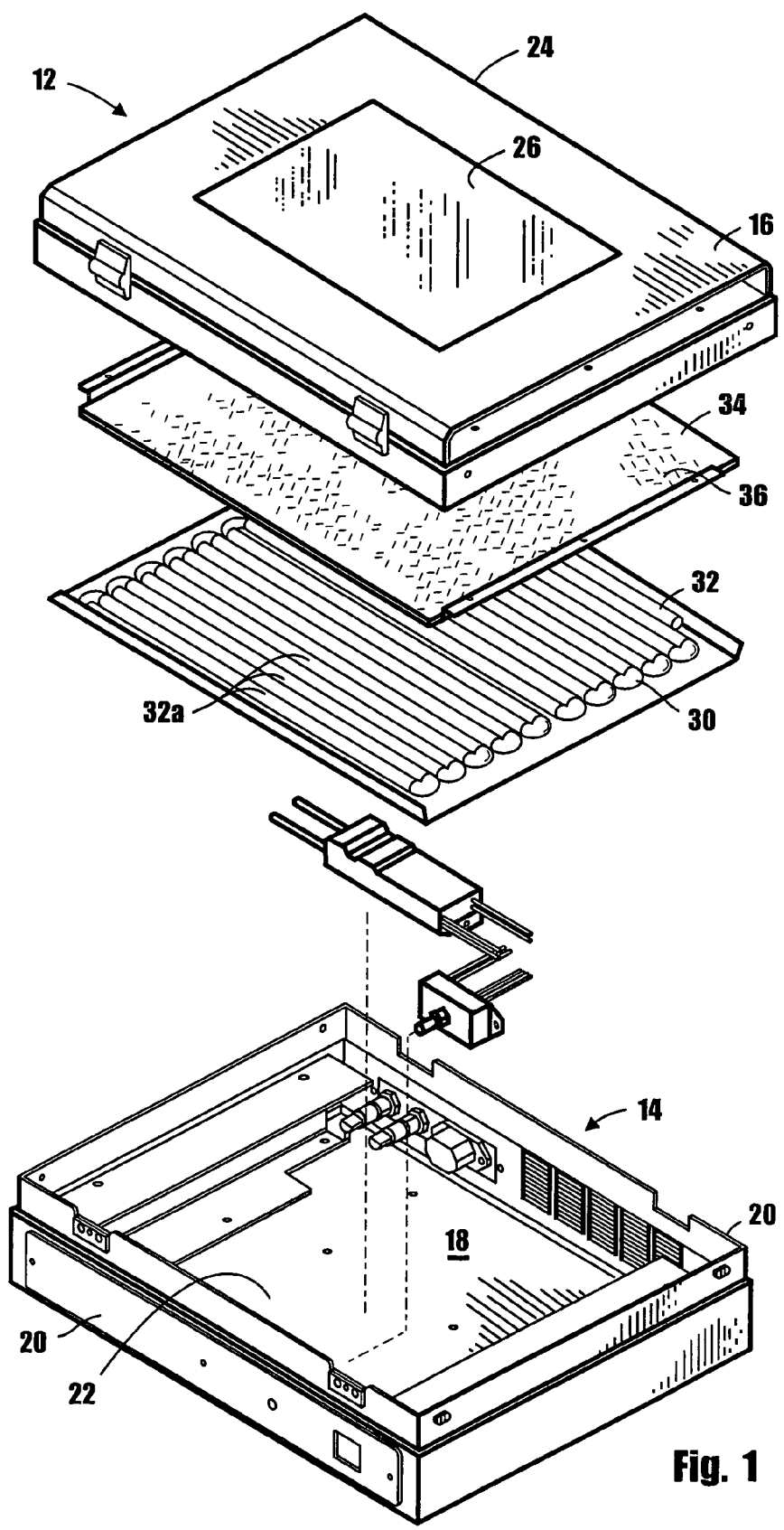
FIG. 1 is a generally perspective, exploded view of one form of the apparatus of the invention for uniformly illuminating molecular samples with ultraviolet radiation.

Referring to the drawings and particularly to FIG. 1, one form of the apparatus of the invention for uniformly illuminating molecular samples with ultraviolet radiation is there shown in and generally designated by the numeral 12. The apparatus of this form of the invention comprises a housing 14 having interconnected top, bottom and sidewalls 16, 18, and 20 respectively that define an internal chamber 22. Carried by top wall 16 is a sample supporting platform 24 having a sample supporting area or surface 26.

An important aspect of the apparatus of the present invention comprises radiation means disposed within chamber 22 for uniformly irradiating the sample supporting area with ultraviolet light at a first wavelength. This novel radiation means here comprises a uniquely configured grid 30 for uniformly emitting ultraviolet radiation. Grid 30 is here constructed from a continuous, serpentine shaped ultraviolet producing tube 32 that is strategically formed to provide a multiplicity of side-by-side, immediately adjacent irradiating segments 32a. As will be discussed in greater detail hereinafter, grid 30 is custom-designed and constructed to uniquely provide in conjunction with the conversion and dispersion means of the invention, a uniform illumination of the sample supporting area which is of the character illustrated in FIG. 3 of the drawings.

Figure 2:
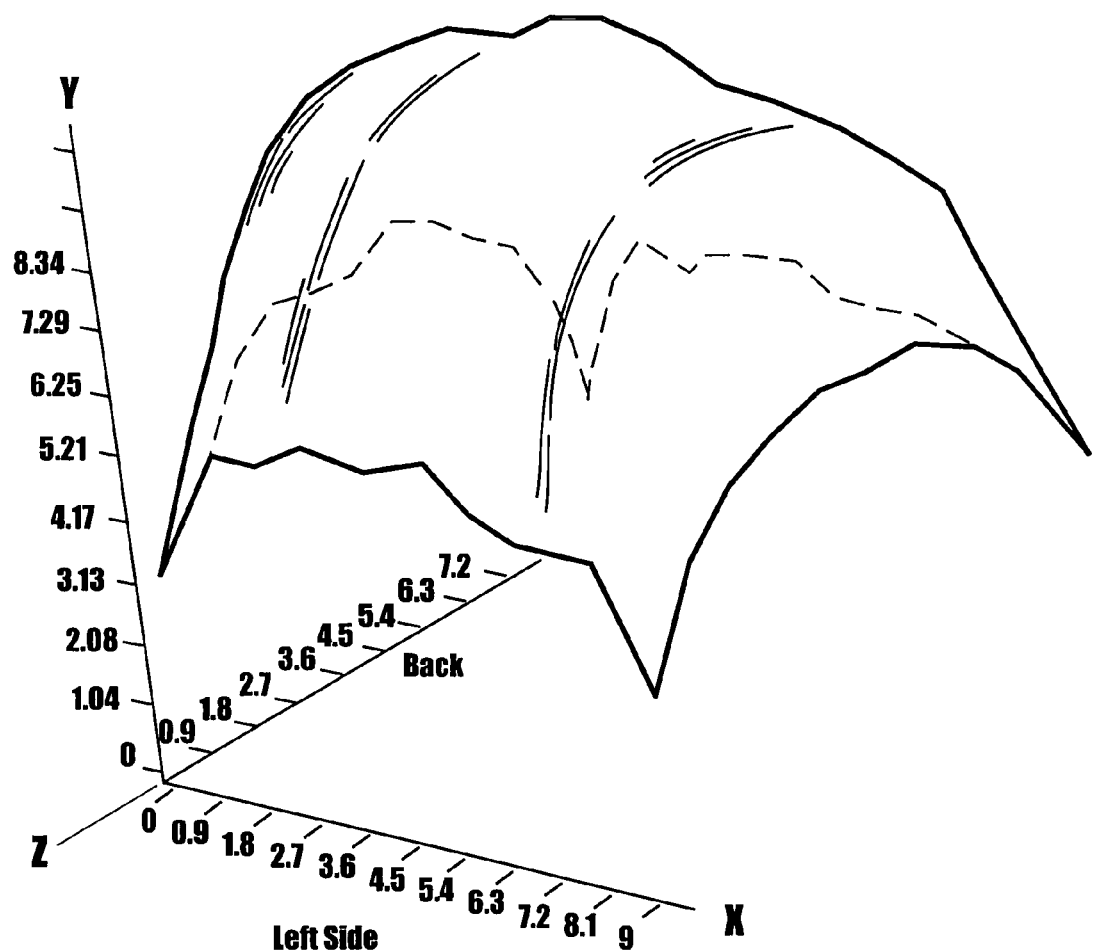
FIG. 2 is a generally perspective, diagrammatic view illustrating of the non-uniform illumination of a sample supporting surface by a conventional, prior art transilluminator using a plurality of standard, side-by-side fluorescent type UV lamps.
Figure 3:
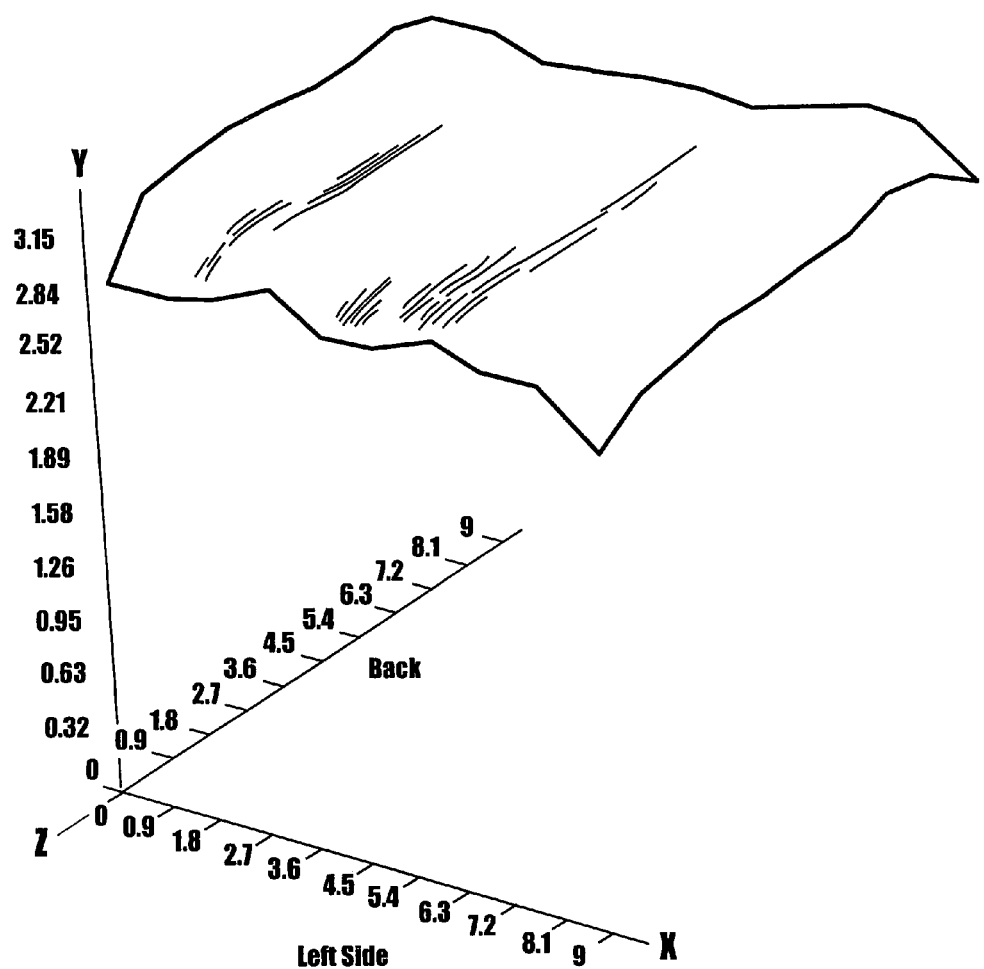
FIG. 3 is a generally perspective, diagrammatic view illustrating the uniform illumination of a sample supporting surface by the uniquely configured ultraviolet radiation emitting grid of the apparatus of the present invention.

By comparing the illumination pattern of a prior art transilluminator is illustrated in FIG. 2 of the drawings, with the illumination pattern of the apparatus of the present invention as illustrated in FIG. 3 of the drawings, it is at once apparent that the uniquely configured grid 30 of the apparatus of the present invention when combined with the conversion and dispersion means of the invention produces a vastly superior illumination of the sample supporting area than does the conventional transilluminator which embodies a plurality of standard, side-by-side fluorescent tubes.

An important aspect of the apparatus of the present invention is the previously mentioned, first conversion means that it is carried by housing 14 at a location intermediate the radiation means, or grid 30, and the superimposed supporting surface 26 platform 24. This important first conversion means functions to convert the radiation emitted from the source of ultraviolet radiation, or grid 30 at a first wavelength of, for example 254 nanometers, to radiation at a second wavelength. This first wavelength conversion means here comprises a conversion plate 34 that is carried within the internal chamber of housing 14 at a location intermediate the sample supporting platform and the UV source 30. More particularly, plate 34 is provided with a conventional wave shifting phosphor coating 36. As is well known in the art, phosphors are compounds that are capable of emitting useful quantities of radiation in the visible and/or ultraviolet spectrums upon excitation of the material by an external energy source. Due to this property, phosphor compounds have long been utilized in cathode ray tube (CRT) screens for televisions and similar devices. Typically, inorganic phosphor compounds include a host material doped with a small amount of an activator ion. In recent years, phosphor compounds, including phosphors in particular form, have been used in display devices, decorations, cathode ray tubes and fluorescent lighting fixtures. Luminescence or light emission by phosphor particles may be stimulated by application of heat (thermo luminescence), light (photo luminescence), high energy radiation (e.g., x-rays or e-beams), or electric fields (Electro luminescence).

A comprehensive discussion of various types of phosphors can be found in U.S. Pat. No. 6,193,908 issued to Hampden-Smith et al.

Figure 4:
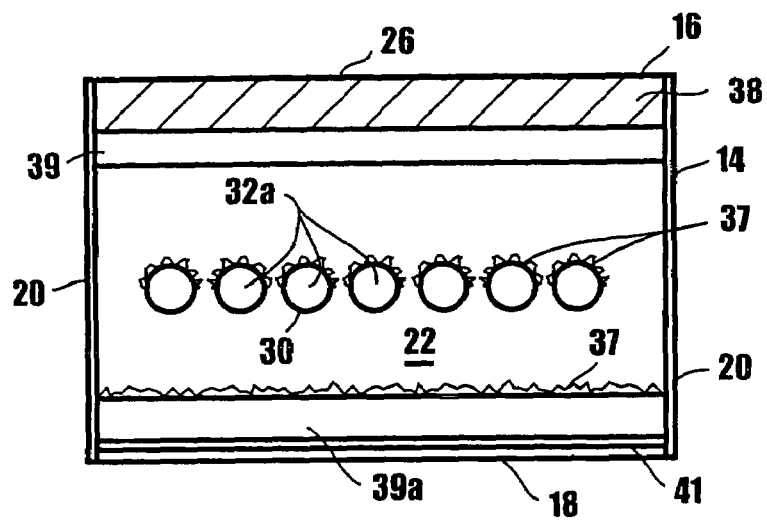
FIG. 4 is a generally diagrammatic, cross-sectional view of an alternate form of the apparatus of the invention.
Figure 5:
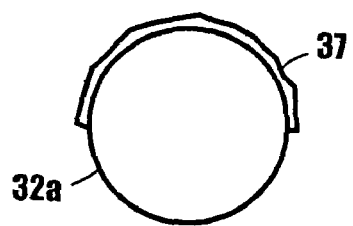
FIG. 5 is a greatly enlarged cross-sectional view of one of the grid segments of the radiation grid of the apparatus showing the segment coated with a phosphor coating.

Referring next to FIGS. 4 and 5, still another form of transilluminator of the invention is there shown in generally diagrammatic form. This embodiment of the invention is also similar in many respects to that shown in FIG. 1 and like numerals are used in FIGS. 4 and 5 to identify like components. This alternate form of the invention comprises a housing 14 having interconnected top, bottom and sidewalls 16, 18 and 20 respectively that define an internal chamber 22. As before, top wall 16 includes a sample supporting area 26.

Positioned between the radiation means or grid 30, are first and second wavelength conversion means which are adapted to convert the UV radiation at the first wavelength of for example, 254 nanometers and then to UV radiation at a second wavelength of, for example 302 nanometers. This first wavelength conversion means here comprises a phosphor coating 37 on the upper surface of each of the grid segments 32a. The second wavelength conversion means here comprises a U.V. transmitting white light blocking filter 38 that is carried by a first borosilicate plate 39 which is located intermediate the sample support area and the grid 30. As well as understood by those skilled in the art, borosilicate does not block visible light or infrared, but does minimize 254 nm U.V.

Also forming a part of the apparatus of this latest form of the invention is a reflector 41, which is carried by the bottom wall of housing 14. Superimposed over reflector 41 is a second borosilicate plate 39a which is coated with a phosphor coating 37. With this construction grid 30 irradiates the phosphor coating on the borosilicate second borosilicate plate 39a converting the 254 nanometer radiation to 302 nanometers. The 302 nanometer radiation radiates upwardly and downwardly, passes through the plate 39a and impinges upon reflector 41. Reflector 41 then reflects the radiation in an upwardly direction through plate 39 and upwardly of chamber 22. The reflected radiation is added to the radiation produced by the phosphor that coats the upper half of the segments of the grid, the upward radiation generated by means of plate 39a and all the combined radiation passes upwardly through filter 38 and impinges on the samples resting on the sample supporting or surface area 26.

Figure 6:
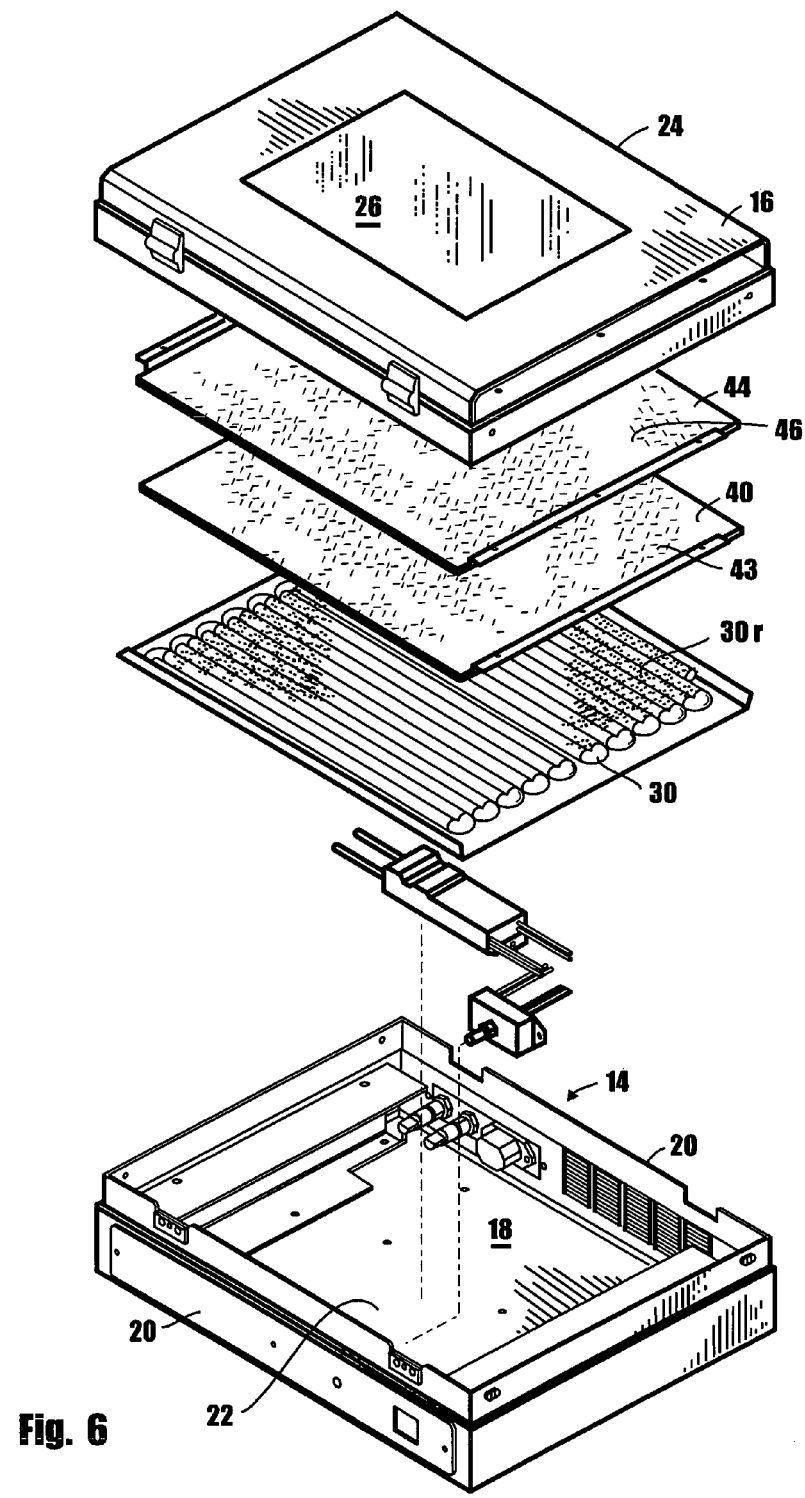
FIG. 6 is a generally perspective, exploded view of an alternate form of the apparatus of the invention for uniformly illuminating molecular samples with ultraviolet radiation.

Referring next to FIG. 6, still another form of transilluminator of the invention is there shown in generally diagrammatic form. This embodiment of the invention is also similar in many respects to that shown in FIG. 1 and like numerals are used in FIG. 6 to identify like components. This alternate form of the invention comprises a housing 14 having interconnected top, bottom and sidewalls, 16, 18 and 20 respectively that define an internal chamber 22. As before, top wall 16 includes a sample supporting area 26.

Positioned between the radiation means, or grid 30, are first and second wavelength conversion means which are adapted to convert the UV radiation at the first wavelength of for example, 254 nanometers to UV radiation at a second wavelength of, for example, 302 nanometers and then to UV radiation at a third wavelength of, for example, 365 nanometers. This first wavelength conversion means here comprises a first conversion plate 40 that is carried by housing 14 at a location intermediate the sample support platform and the grid 30. In this instance, plate 40 is provided with a wave shifting phosphor coating 43. The second wavelength conversion means of this latest form of the invention comprises a second conversion plate 44 that is also carried by housing 14 at a location between conversion plate 40 and sample supporting platform 24. Plate 44 is provided with a wave shifting phosphor coating 46. It is to be understood that, with the construction shown in figure 6, either or both plates 40 and 44 can be removed from the housing and replaced with alternate plates if desired.

As illustrated in FIG. 6, the tubes of the grid 30 are roughened, or abraded to disperse the UV radiation being emitted therefrom. The surfaces of the tubes can be roughened by various means including chemical etching, sandblasting, mechanical lapping and like types of mechanical abrading.

This roughened surfaces 30r function to disperse the UV, in a manner to significantly contribute to the uniform illumination of sample supporting platform 24.

Figure 7:
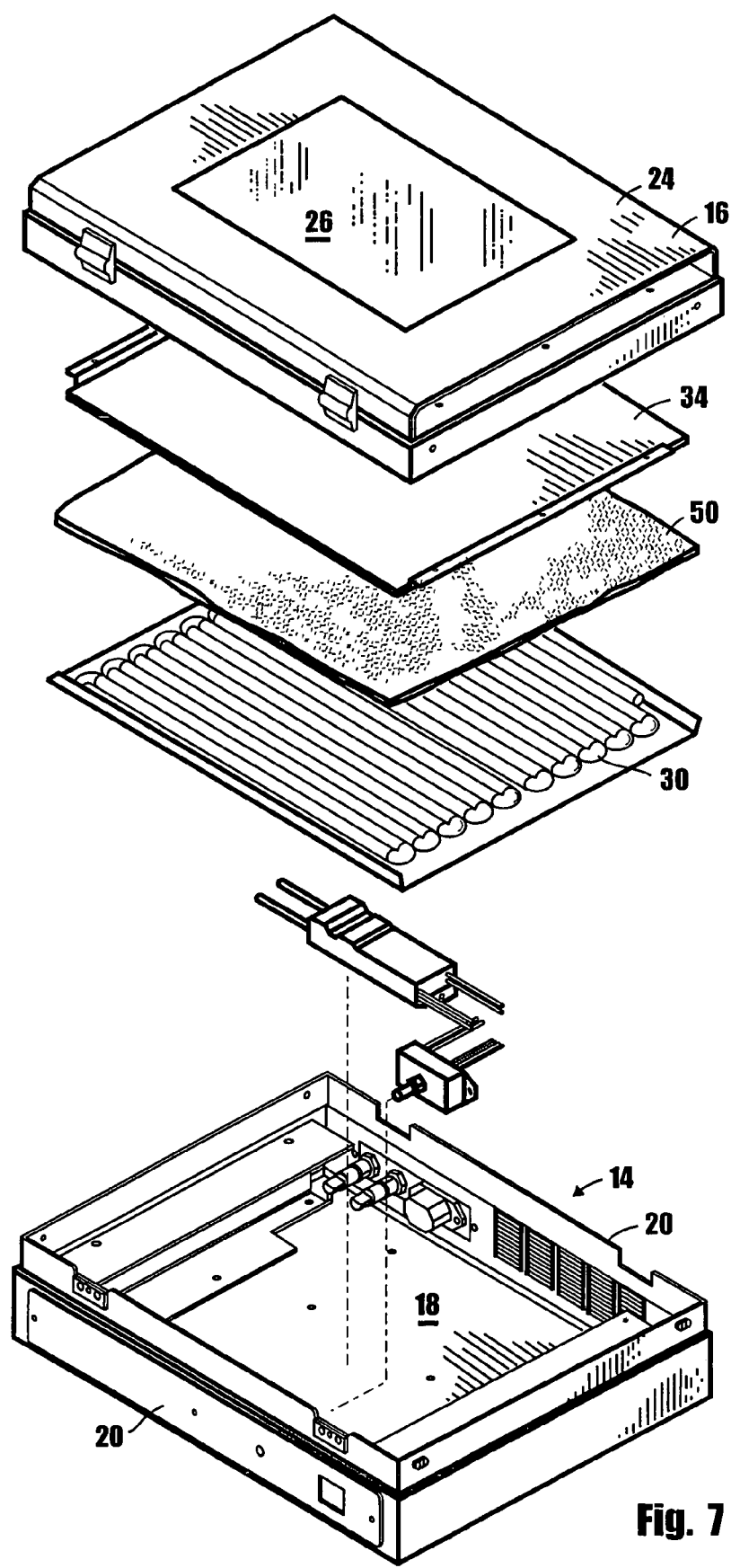
FIG. 7 is a generally perspective, exploded view of still another form of the apparatus of the invention for uniformly illuminating molecular samples with ultraviolet radiation.

Turning to FIG. 7, still another embodiment of the invention is there shown. This form of the invention is also similar in many respects to that shown in FIG. 7, and like numerals are once again used to identify like components. This alternate form of the invention comprises a housing 14 having interconnected top, bottom and sidewalls 16, 18 and 20. Carried by top wall 16 is a sample supporting platform 24 having a sample supporting area 26.

As illustrated in FIG. 7 of the drawings, the UV source once again comprises the uniquely configured grid 30 that emits UV radiation at a first wavelength of, for example, 254 nanometers. Positioned between grid 30 and the sample-supporting platform 24 is the novel dispersion means, here comprising a quartz fibrous mesh 50. This novel dispersion means, or fibrous mesh 50, functions to uniformly disperse the radiation generated by grid 30 in a manner to significantly contribute to the uniform illumination of the sample supporting platform 24. Disposed intermediate the dispersion means and the sample supporting platform 24 is a first wavelength conversion means, or conversion plate 34 that is carried within the internal chamber of housing 14 at a location intermediate the sample supporting platform and the fibrous mesh 50. More particularly, plate 34 which is of the character previously described, is adapted to convert the UV radiation at the first wavelength of about 254 nanometers to UV radiation at a second wavelength.

Turning once again to FIG. 2, this drawing comprises a graphical representation of the nonuniform illumination of the sample supporting platform which results from ultraviolet radiation emitted from a conventional transilluminator having six side-by-side, elongated tubular shaped lamp radiation sources (distances along the left and backside of the sample supporting platform are represented by the X and Y axes in FIG. 2, while radiation intensity is represented by the Z axis). The data shown in FIG. 2 was obtained using a bench top transilluminator manufactured and sold by UVP, Inc., of Upland, Calif. under the model designation M26X. This transilluminator uses six F8T5 302 nm 8-watt lamps and embodies a 25 cm×26 cm UV transmitting, ambient (visible light) blocking filter.

Figure 8:
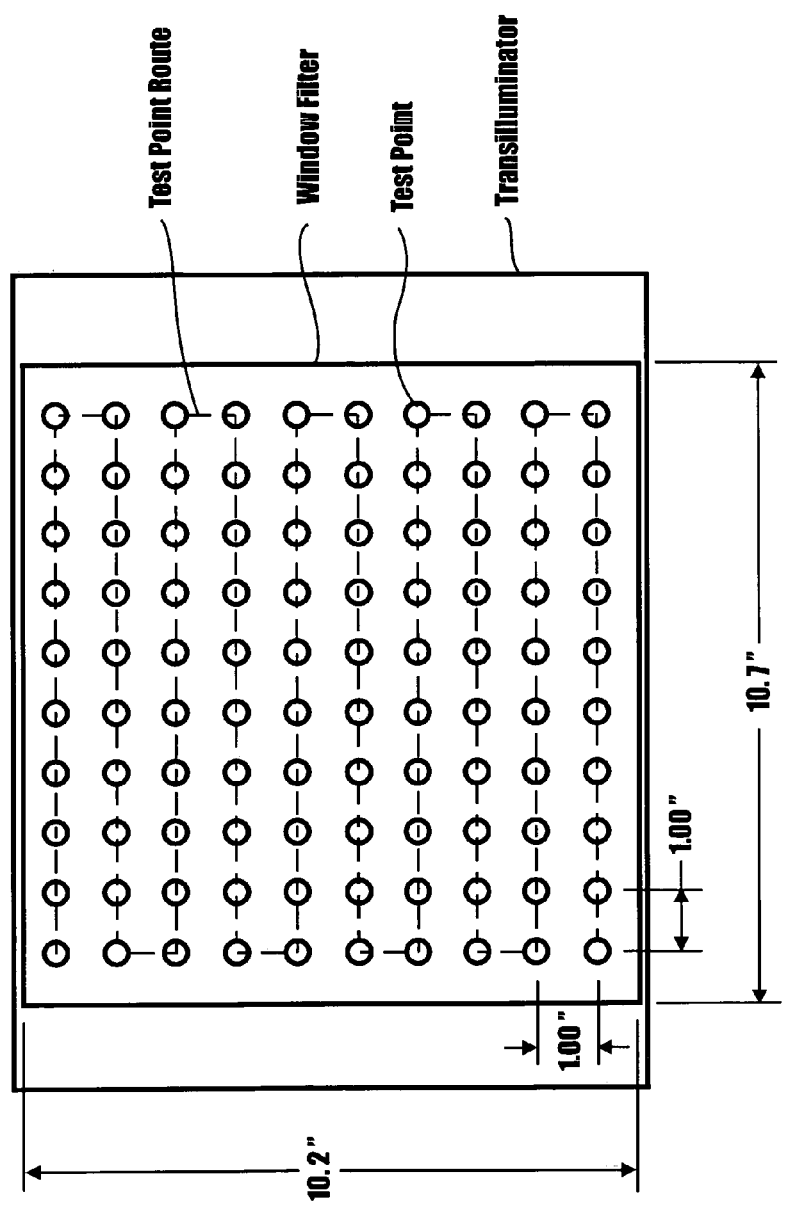
FIG. 8 is a generally diagrammatic view illustrating the manner in which the data shown in FIGS. 2 and 3 was obtained.

The data represented in FIG. 2 was obtained by measuring the intensity of the 302 nm radiation emitted by the ultraviolet lamps at 100 equally spaced (one inch apart) points 1.5 mm from the filter surface (see FIG. 8). The sensor used was a UVP, Inc. Model UVX-31 radiometer. The sensor was placed on each of the 100 points for 5 seconds and the intensity was recorded. The intensity of 185 nm radiation emitted by the lamps was measured in the center of the filter at a location 2 mm above the surface. The sensor used was a sensor that is commercially available from International Light of Newbury Port, Mass. under the model designation IL1700. In this instance the sensor was outfitted with a model SEE220 sensor head. This latter measurement was used to estimate the relative levels of ozone production.

As clearly shown in FIG. 2, the radiation intensity falls off markedly from the center of the sample supporting surface to the edges thereof In the prior art of transilluminating, the excitation light intensity is thus dependent on position of the sample on the sample-supporting platform, making quantitative side-by-side and sequential comparisons extremely difficult. Accordingly, the same sample will give very different fluorescent intensities depending on where the sample is placed on the sample-supporting platform of the typical prior art transilluminator.

FIG. 3 comprises a graphical representation of the substantially uniform illumination of the sample-supporting platform of the present invention, which results from ultraviolet radiation emitted from the uniquely configured radiation sources, or grid 30 of the apparatus. FIG. 3 clearly illustrates the dramatic improvement in the uniformity of excitation radiation across the sample supporting surface area 26 of the apparatus of the present invention when compared with the nonuniformity of radiation across the sample-supporting surface of the prior art transilluminator. With the coefficient of variation of CV well below about 5 to 10% as illustrated in FIG. 3, meaningful, quantitative side-by-side comparisons are quite possible using the apparatus of the present invention. In addition, sequential analysis of several samples is also simplified and is substantially more accurate because of the minimal effect sample placement position has on excitation intensity. Stated another way, the sample will give substantially similar fluorescent intensities regardless of where the sample is positioned on the sample-supporting platform of the apparatus of the present invention.

In obtaining the data used to plot the graphical representations shown in FIGS. 2 and 3, the average intensity was calculated using the following formula:

$$\text{Output} = \frac{\sum_{i=1}^{n} X_i}{n}$$

The percent uniformity is the average of the row and column uniformity. This uniformity was calculated using the following formula:

Row uniformity=1−the tolerance of the row test point divided by the mean of the row test points (10).

Column uniformity=1−the tolerance of the column test point divided by the mean of the column test points (10)

Thus:

$$\text{Uniformity} = 1 - \frac{\max - \min}{\overline{X}}, \quad \overline{X} = \frac{\sum_{i=1}^{n} X_i}{n}$$

The Coefficient of Variation (CV) is the standard deviation of the individual data points divided by the average. More specifically, the CV is a relative measure of variation and independent of units, and is ideal for evaluating results from different experiments that use the same basic test or instrument. In this case, variations of the transillumination intensity across various transilluminator designs were quantified and compared. The lower the CV, the smaller the variation of intensity across the active area of the transilluminator.

$$\text{Coefficient of Variation} = \frac{s}{\overline{X}}$$

$$s = \sqrt{\frac{\sum_{i=1}^{n}(X_i - \overline{X})^2}{n-1}}$$

$$\overline{X} = \sum_{i=1}^{n} \overline{X}_i$$

It is to be noted that the Coefficient of Variation times 100 = percentage.

A study of FIGS. 2 and 3 clearly demonstrates the value of the present invention and the substantial advancement over the prior art that it represents.

Figure 9:
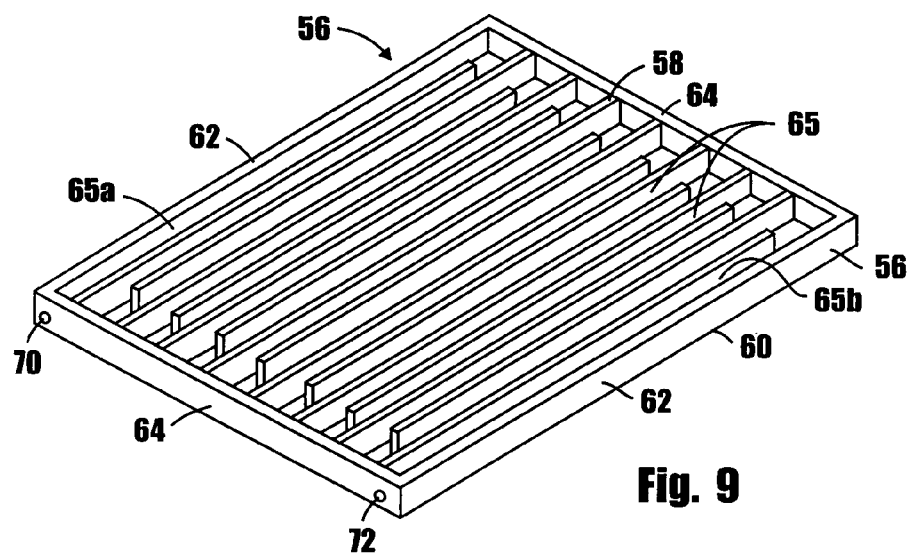
FIG. 9 is a generally perspective, view of the base portion of an alternate form of the radiation means of the apparatus of the invention for uniformly illuminating molecular samples with ultraviolet radiation.
Figure 10:
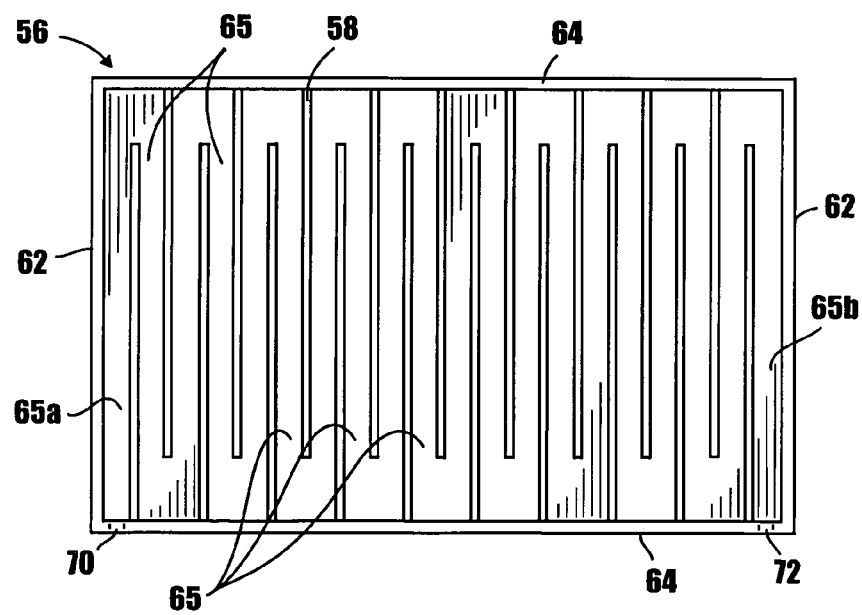
FIG. 10 is a top plan view of the base portion of the radiation means shown in FIG. 9.
Figure 11:
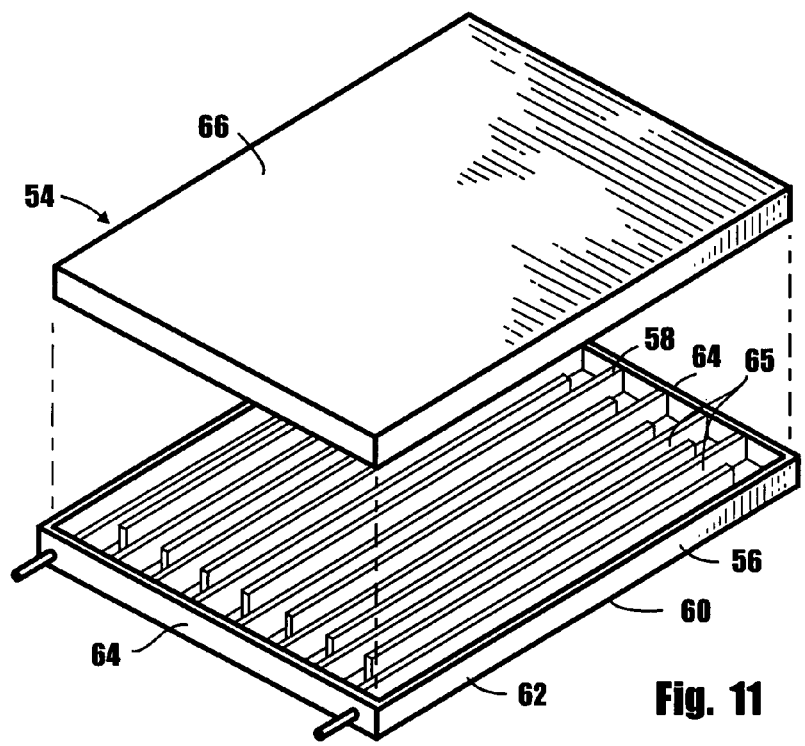
FIG. 11 is a generally perspective, exploded view of the alternate form of radiation means form of the apparatus of the invention showing the cover plate of the radiation means superimposed over the grooved base portion shown in FIG. 9.

Turning to FIGS. 9 through 11, an alternate form of the radiation means of the invention for uniformly illuminating molecular samples with ultraviolet radiation in the range between about 150 to 395 nm. This novel radiation means can take the place of the previously described grid 30 and provides, in conjunction with the conversion means of the invention, uniform illumination of the sample supporting area of the apparatus, such as the area 26 illustrated in FIG. 3 of the drawings.

As illustrated in FIGS. 9, 10 and 11 the unique radiation means of this latest form of the invention compromises an irradiation assembly 54 (FIG. 11) which includes a blocklike base 56 having interconnected top, bottom, side and end walls 58, 60, 62 and 64 respectively. Base 56 can be constructed from a variety of machinable materials, but preferably is constructed of a borosilicate material. As best seen in FIG. 10, top wall 58 is strategically milled in a conventional manner to form a plurality of interconnected channels 65.

Figure 12:
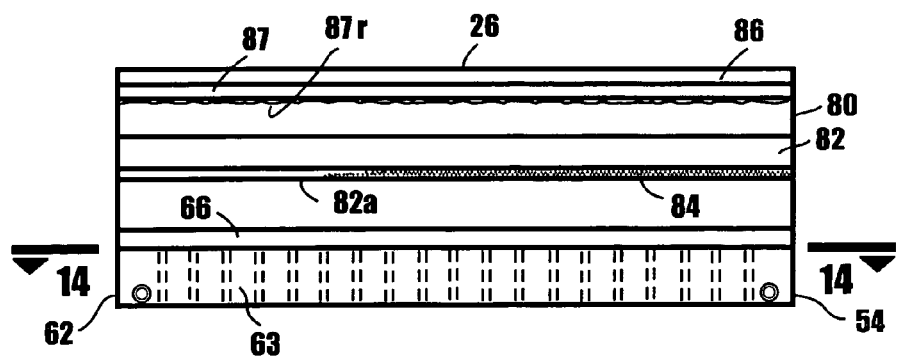
FIG. 12 is a generally diagrammatic, cross-sectional view of the principal components of yet another form of the apparatus of the invention for illuminating samples with ultraviolet radiation.
Figure 13:
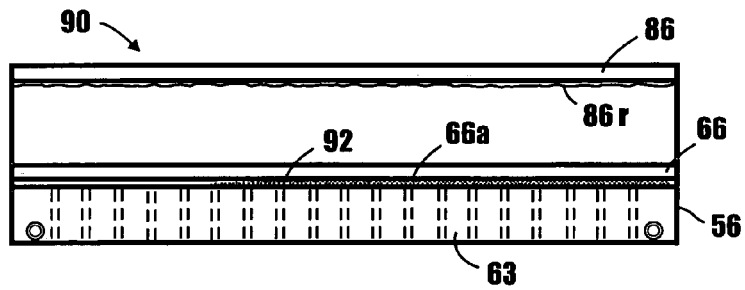
FIG. 13 is a generally diagrammatic, cross-sectional view of the principal components of still another form of the apparatus of the invention for illuminating samples with ultraviolet radiation.
Figure 14:
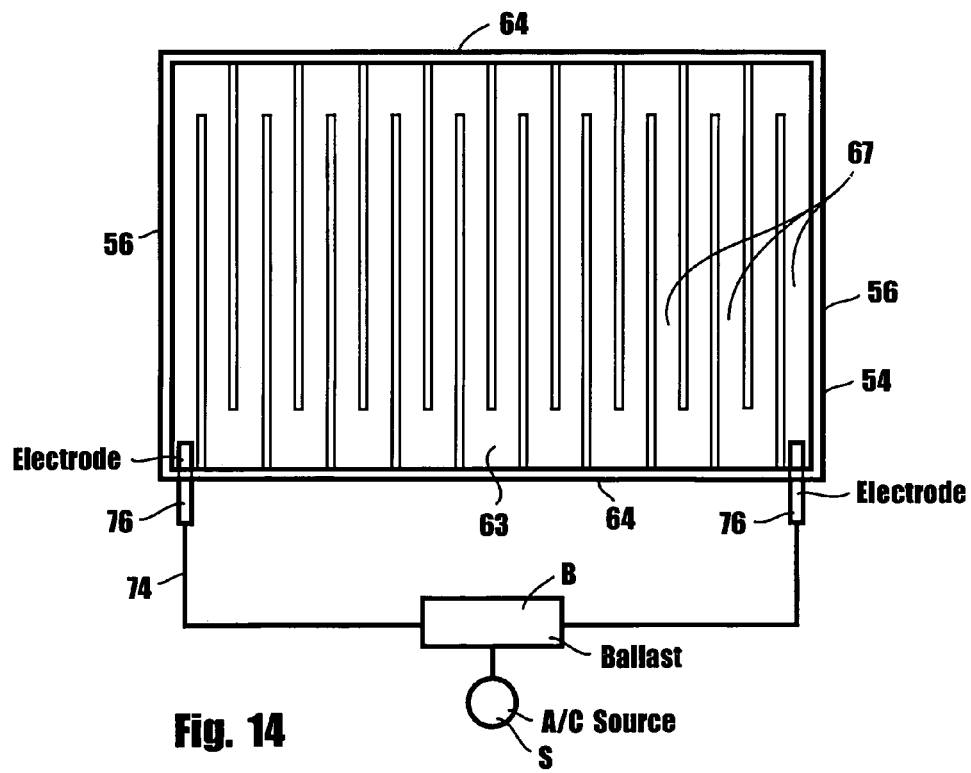
FIG. 14 is a generally diagrammatic, cross-sectional view taken along lines 14—14 of FIG. 12.

Over laying milled base is a top plate 66 which cooperates with the base to form irradiation assembly 54, which as shown in FIGS. 12 and 13, includes a generally serpentine shaped pathway 63 comprising plurality of closed channels 67 (FIG. 14). Top plate 66 is sealably interconnected with the top surface 58 of base 56 by any suitable means, such as adhesive bonding. As best seen in FIGS. 9 and 10, the end wall 64a of base 56 is provided with a pair of spaced apart bores 70 and 72. Bore 70 communicates with channel 65a, which is located proximate one side and the base, and bore 72 communicates with channel 65b, which is located proximate the opposite side of the base. Suitable electrical conduits 74, which are connected to conventional electrodes 76 (FIG. 14) extend through bores 70 and 72.

After top plate 66 is sealably connected to base 56, a conventional pump can be interconnected with bores 70 and 72 and can be used to evacuate pathway 63. This done, bores 70 and 72 can be used to fill the sealed pathway 63 with a suitable gaseous medium and the bores can be appropriately sealed in a manner well understood by those skilled in the art to retain the gaseous medium within the closed channels.

Depending upon the end use to be made of the irradiation means, the gaseous medium can comprise mercury, metal halides and various inert gases, such as xenon, argon and neon. As illustrated in FIG. 14, the electrodes 76, which are provided at either end of pathway 63, are interconnected with a source of alternating current "S" via a suitable ballast "B". As in conventional fluorescent tubes, when voltage is applied across the electrodes, some of the mercury in the gaseous pathway will be changed from a liquid to a gas. As the electrons and charged atoms move through the gaseous pathway, some of them will collide with the gaseous mercury atoms. These collisions excite the atoms of the electrons up to higher energy levels. When the electrons return to their original energy level they will release light photons. As in conventional ultraviolet sources, the electrons in the mercury atoms are arranged in such a way that they mostly release photons in the ultraviolet wavelength and, in this instance, in a wavelength of on the order of the 254 nm.

Turning next to FIGS. 12 and 14, it can be seen that the apparatus of this latest form of the invention is also similar in many respects to that shown in FIG. 1 and like numerals are used in FIG. 12 to identify like components. This alternate form of the invention includes a first conversion means that is carried with a housing 80, which is of a similar construction to the earlier described housing 20. This first conversion means is here provided as a borosilicate transmitting plate 82 having a 302 nm. phosphor coating 84 provided on the lower surface 82a of the transmitting plate. As indicated in FIG. 12, plate 82, which is located intermediate the radiation means, or irradiation assembly 54 and the sample supporting area 26, functions to convert the radiation emitted from the irradiation assembly 54 to radiation at a second wavelength. In this latest embodiment of the invention the irradiation means emits radiation at a wave length of about 254 nanometers and the first conversion means converts the radiation to approximately 365 nanometers.

It is to be understood that the lower surface 82a of the transmitting plate can also be coated with 365 nm phosphor or alternatively a combination of 302 nm and 365 nm phosphor. If the lower surface of the transmitting plate is coated with 365 nm phosphor, the 254 nm radiation emitted from the radiation means will be converted to approximately 365 nanometers.

Also forming a part of this latest form of the apparatus of the invention is an ultraviolet transmitting filter 86 which is superimposed over transmitting plate 82 in the manner shown in FIG. 12 of the drawings. Disposed between filter 86 and plate 82 is a glass plate 87. The lower surface of plate 87 is roughened, or abraded to provide a roughened surface 87r which functions to uniformly disperse the UV radiation being emitted from the radiation source. This dispersion of the radiation contributes to the uniform illumination of sample supporting platform 24 and the examples resting thereon.

Turning next to FIG. 13, still another form of the apparatus of the invention is there shown and generally designated by the numeral 90. This form the invention is also similar in many respects to that shown in FIG. 1 and like numerals are used in FIG. 13 to identify like components. In this last form of the invention top plate 66 is provided on its lower surface 66a with a 302 nm. phosphor coating 92. With this construction, the plate assemblage comprises the first conversion means of the invention for converting the radiation emitted from the gaseous medium within pathway 62 to radiation at a second wavelength. In this latest embodiment of the invention the gaseous medium within pathway 63 emits radiation at a wave length of about 254 nanometers and the first conversion means converts the radiation to approximately 302 nanometers.

It is to be understood that the lower surface 66a of the cover plate can also be coated with 365 nm phosphor or alternatively a combination of 302 nm and 365 nm phosphor. If the lower surface of the cover plate is coated with 365 nm phosphor, the 254 nm radiation emitted from the air radiation means will be converted to approximately 365 nanometers.

Also forming a part of the embodiment of the invention shown in FIG. 13 is an ultraviolet transmitting filter 86 which is superimposed over cover plate 66 in the manner shown in FIG. 13 of the drawings. The lower surfaced filter 86 is roughened in the manner previously described to provide a roughened, or abraded surface 86r that functions to uniformly disperse the UV radiation being emitted by radiation source. This dispersion of the UV significantly contributes to the uniform illumination of the sample supporting platform 24.

It is to be understood that plates 66 and 82 could also be constructed from glass rather than borosilicate and that various types of phosphor could be used to coat the surfaces of the plates.

Referring next to FIGS. 15 and 16, still another embodiment of present the invention is there shown and generally designated by the numeral 94. This embodiment of the invention is also similar in many respects to that shown in FIG. 1 and like numerals are used in FIGS. 15 and 16 to identify like components. This alternate form of the invention comprises a housing 14 having interconnected top, bottom and sidewalls 16, 18 and 20 respectively that define an internal chamber 22. As before, top wall 16 includes a sample supporting area 26.

As illustrated in FIG. 15 of the drawings, the UV source once again comprises the uniquely configured grid 30 that emits UV radiation at a first wavelength of, for example, 254 nanometers.

Positioned between grid 30 and the sample-supporting platform 24 is the previously mentioned dispersion means of the invention, which here comprises a flat plate 96 which is constructed from a glass or similar material having an upper surface 96a and a lower surface 96b. As indicated in FIGS. 16 and 17, upper surface 96a is roughened or abraded in a manner to uniformly disperse the radiation generated by grid 30 as the radiation passes through the plate 96. Surface 96a can be formed by various means including chemical etching, sandblasting and numerous mechanical abrading techniques well understood by those skilled in the art. This important roughening of upper surface 96a of plate 96 effectively disperses the radiation passing through the plate and significantly contributes to the uniform illumination of the sample supporting platform 24.

In this latest embodiment of the invention, lower surface 96b of plate 96 is coated with a phosphor coating generally designated in FIG. 16 by the numeral 98. In the manner previously discussed herein, the phosphor coating 98 functions to convert the UV radiation emitted from the radiation source at the first wavelength of about 254 nanometers to UV radiation at a second wavelength thereby making plate 96 a combination dispersion and wavelength conversion means for both disbursing the radiation passing through the plate and for converting the radiation from a first wavelength to a second wavelength.

Referring next to FIGS. 17 and 18, still another embodiment of present the invention is there shown and generally designated by the numeral 104. This embodiment of the invention is also similar in many respects to that shown in FIG. 1 and like numerals are used in FIGS. 17 and 18 to identify like components. This alternate form of the invention comprises a housing 14 of the same construction and operation as that previously described and further includes a UV radiation source in the form of the previously described grid 30.

Positioned between grid 30 and the sample-supporting platform 24 is still another form of the dispersion means of the invention. This latest form of the dispersion means comprises a flat plate 106 which is constructed from a glass or similar material having an upper surface 106a and a lower surface 106b. As indicated in FIGS. 17 and 18, both the upper surface 106a and a lower surface 106b are roughened or abraded in the manner previously described. Accordingly, plate 106 once again functions to uniformly disperse the radiation generated by grid 30 as the radiation passes through the plate 106. In this latest embodiment of the invention surface 106b is also coated with a phosphor coating 107. As before, the phosphor coating 107 functions to convert the UV radiation emitted from the radiation source at the first wavelength of about 254 nanometers to UV radiation at a second wavelength thereby making plate 107a combination dispersion and wavelength conversion means for both disbursing the radiation passing through the plate and for converting the radiation from a first wavelength to a second wavelength.

Referring next to FIGS. 19, 20 and 21 still another embodiment of present the invention is there shown and generally designated by the numeral 110. This embodiment of the invention is also similar in many respects to that shown in FIG. 1 and like numerals are used in FIGS. 19 through 21 to identify like components. This alternate form of the invention comprises a housing 14 of the same construction and operation as that previously described and further includes a UV radiation source in the form of the previously described grid 30.

Positioned between grid 30 and the sample-supporting platform 24 is still another form of the dispersion means of the invention. This latest form of the dispersion means comprises a flat plate 112 which is constructed from a glass or similar material having an upper surface 112a and a lower surface 112b. As indicated in FIGS. 19 and 20, upper surface 112a is roughened or abraded in the manner previously described herein and once again functions to uniformly disperse the radiation generated by grid 30 as the radiation passes through the plate 112. In this latest embodiment of the invention surface 112b is untreated. However it is to be understood that for certain applications surface 112b can also be roughened or abraded in a suitable manner. In either case, plate 112 effectively disperses the radiation passing through the plate and significantly contributes to the uniform illumination of the sample supporting platform 24.

Positioned between plate 112 and grid 30 is a wavelength conversion means, or conversion plate 114 that is carried within the internal chamber of housing 14 in the manner indicated in FIG. 19. Plate 114 which is of the character previously described has an upper surface 114a and a lower surface 114b that is coated with a phosphor generally designated in FIG. 21 by the 115. As before the phosphor coating 115, is adapted to convert the UV radiation emitted from the grid 30 at the first wavelength of about 254 nanometers to UV radiation at a second wavelength.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for uniformly illuminating molecular samples with ultraviolet radiation comprising:
    (a) a housing including an internal chamber and a sample supporting platform having a sample supporting area;
    (b) irradiation means disposed within said chamber for uniformly irradiating said sample supporting area with ultraviolet light at a first wavelength, said irradiation means comprising an irradiation assembly including:
        (i) a base having interconnected top, bottom and side walls, said top wall having a plurality of interconnected, top open channels formed therein;
        (ii) a top plate overlaying said base and cooperating therewith to form a plurality of closed channels; and
        (iii) a gaseous medium contained within said closed channels.

2. The apparatus as defined in claim 1 further including a first conversion means removably carried by said housing at a location intermediate said irradiation means and said sample supporting platform for converting the radiation emitted from said irradiation means to radiation at a second wavelength.

3. The apparatus as defined in claim 2 in which said irradiation means emits radiation at a wave length of about 254 nanometers and in which said first conversion means converts the radiation to approximately 365 nanometers.

4. The apparatus as defined in claim 2 in which said irradiation means emits radiation at a wave length of about 254 nanometers and in which said first conversion means converts the radiation to approximately 300 nanometers.

5. The apparatus as defined in claim 1 in which said gaseous medium comprises argon.

6. The apparatus as defined in claim 1, in which said gaseous medium comprises xenon.

7. The apparatus as defined in claim 1, in which said gaseous medium comprises neon.

8. The apparatus as defined in claim 1, in which said gaseous medium comprises mercury.

9. The apparatus as defined in claim 1, in which said gaseous medium comprises a metal halide.

10. The apparatus as defined in claim 1 in which said top platehas an upper surface and a lower surface coated with phosphor.

11. An apparatus for uniformly illuminating molecular samples with ultraviolet radiation comprising:
    (a) a housing including an internal chamber and a sample supporting platform having a sample supporting area;
    (b) irradiation means disposed within said chamber for uniformly irradiating said sample supporting area with ultraviolet light at a first wavelength, said irradiation means comprising an irradiation assembly including:
        (i) a base having interconnected top, bottom side and end walls, said top wall having a plurality of interconnected, top open channels machined therein;
        (ii) a top plate overlaying said base and cooperating therewith to form a plurality of closed channels defining a generally serpentine shaped pathway; and
        (iii) a medium comprising mercury and argon contained within said pathway.

12. The apparatus as defined in claim 11 further including a first conversion means removably carried by said housing at a location intermediate said irradiation means and said sample supporting platform for converting the radiation emitted from said irradiation means to radiation at a second wavelength.

13. The apparatus as defined in claim 11 in which said top plate has an upper surface and a lower surface coated with phosphor.

14. The apparatus as defined in claim 11 in which one of said end walls of said base has spaced apart bores formed therein and in which said irradiation means further includes electrodes mounted within said bores.

15. The apparatus as defined in claim 14 in which said irradiation means further includes a source of electric current and an electrical conduit interconnecting said electrodes with said source of electric current.

16. An apparatus for uniformly illuminating molecular samples with ultraviolet radiation comprising:
    (a) a housing including an internal chamber and a sample supporting platform having a sample supporting area;
    (b) radiation means disposed within said chamber for emitting ultraviolet radiation to uniformly irradiate said sample supporting area with ultraviolet radiation at a first wavelength, said radiation means comprising a grid for emitting ultraviolet radiation constructed from a serpentine shaped ultraviolet tube; and
    (c) dispersion means carried within said internal chamber of said housing for dispersing the radiation emitted from said radiation means.

17. The apparatus as defined in claim 16 in which said dispersion means comprises a plate carried by said housing at a location intermediate said radiation means and said sample supporting platform, said plate having an upper surface and a lower surface, at least one of said upper and lower surfaces being roughened in a manner to disperse the ultraviolet radiation emitted from said radiation means.

18. The apparatus as defined in claim 17 in which said lower surface of said plate is coated with phosphor for converting the ultraviolet light emitted from said radiation means at a first wavelength to ultraviolet light at a second wavelength.

19. The apparatus as defined in claim 18 in which said radiation means emits ultraviolet radiation at a wave length of about 254 nanometers and in which said phosphor converts the radiation to approximately 365 nanometers.

20. The apparatus as defined in claim 17, further including a conversion plate disposed between said plate and said radiation means, said conversion plate having a phosphor coating.

21. The apparatus as defined in claim 16 in which said radiation means comprises a serpentine shaped ultraviolet tube having an upper surface, said ultraviolet tube being strategically formed to provide a multiplicity of side-by-side, immediately adjacent irradiating segments.

22. The apparatus as defined in claim 21 in which said upper surface of said ultraviolet tube is roughened in a manner to disperse the radiation emitted from said ultraviolet tube.

23. An apparatus for uniformly illuminating molecular samples with ultraviolet radiation comprising:
    (a) a housing including an internal chamber and a sample supporting platform having a sample supporting area;
    (b) radiation means disposed within said chamber for emitting ultraviolet radiation to uniformly irradiate said sample supporting area with ultraviolet radiation at a first wavelength, said radiation means comprising a grid for emitting ultraviolet radiation constructed from a serpentine shaped ultraviolet tube;
    (c) a plate carried by said housing at a location intermediate said radiation means and said sample supporting platform, said plate having an upper surface and a lower surface, at least one of said upper and lower surfaces being roughened in a manner to disperse the ultraviolet radiation emitted from said radiation means; and
    (d) a conversion plate disposed between said plate and said radiation means, said conversion plate having a phosphor coating.

24. The apparatus as defined in claim 23 in which said radiation means comprises a serpentine shaped ultraviolet tube having a roughened upper surface for dispersing the radiation emitted from said tube.

\* \* \* \* \*